(12) United States Patent
Foster

(10) Patent No.: US 6,500,182 B2
(45) Date of Patent: *Dec. 31, 2002

(54) MINIMALLY-INVASIVE MEDICAL RETRIEVAL DEVICE

(75) Inventor: Thomas L. Foster, Poland, IN (US)

(73) Assignee: Cook Urological, Incorporated, Spencer, IN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/277,098

(22) Filed: Mar. 26, 1999

(65) Prior Publication Data

US 2001/0041899 A1 Nov. 15, 2001

Related U.S. Application Data

(60) Provisional application No. 60/079,540, filed on Mar. 27, 1998.

(51) Int. Cl.[7] .............................................. A61B 17/22
(52) U.S. Cl. ...................................................... 606/127
(58) Field of Search ................................ 606/110, 114, 606/127, 128; 128/DIG. 24

(56) References Cited

U.S. PATENT DOCUMENTS 2,556,783 A * 6/1951 Wallace ..................... 606/127
4,046,150 A * 9/1977 Schwartz et al. .......... 606/127
4,347,846 A * 9/1982 Dormia ...................... 606/127

(List continued on next page.)

FOREIGN PATENT DOCUMENTS

| DE | 19722429 | 5/1997 | | |
|----|----------|--------|---|---|
| EP | 0512729 | 11/1992 | | |
| EP | 07430456 | 11/1996 | | |
| EP | 0818180a2 | * 1/1998 | ................. | 606/127 |
| EP | 9818180 | 1/1998 | | |
| WO | 9735522a | * 10/1997 | ................. | 606/127 |
| WO | 9739674 | 10/1997 | | |

Primary Examiner—Eduardo C. Robert
(74) Attorney, Agent, or Firm—Brinks Hofer Gilson & Lione

(57) ABSTRACT

A medical retrieval device 10 is disclosed comprising an elongated cylindrical member 11 that includes a continuum of a material 40, preferably a metal such as stainless steel or nitinol, that forms both the resilient grasping members 13 of retrieval basket 54, snare 26, or grasper forceps 23, and the proximal portion 21 or shaft of the device. The elongated cylindrical member can include a metal cannula 60 or solid rod 62 into which a series of laterally adjacent longitudinal slots 15 are cut or formed in the distal portion 37 of the elongated cylindrical member to form a plurality of resilient grasping members. These slots may be cut in a spiral configuration to produce a helical basket 69. The resilient grasping members in the original compact shape 17 are formed into an enlarged shape 18 to create a workspace volume 28 for the capture, manipulation and/or retrieval of an object within a patient. An external constraining device 14, such as an outer sheath, is used for introducing of the device and to compress the resilient grasping members over a calculus 24 or other object into a substantially closed position 30. An internal actuating member 29 within the passage 12 of the elongated cylindrical member can provide an alternative method of opening and closing the retrieval device. Using a small thin-walled cannula, retrieval devices of the present invention can fit through the accessory channel 46 of a small endoscope, such as an ureteroscope 44 while still having a sufficient lumen size to accommodate an ancillary treatment device 25 such as a standard 200 micron laser fiber or lithotripsy wire. The present invention also includes a retrieval device made from a plastic tube 32 having encased reinforcement wires 31. By removing all material 66 except the reinforcement wires from the distal portion of the elongated cylindrical member, the exposed wires can become the resilient grasping members of a basket or forceps.

18 Claims, 5 Drawing Sheets

U.S. PATENT DOCUMENTS

| | | | |
|---|---|---|---|
| 4,393,872 A | | 7/1983 | Reznik et al. |
| 4,607,620 A | | 8/1986 | Storz |
| 4,611,594 A | * | 9/1986 | Grayhack et al. ............ 606/127 |
| 4,625,726 A | | 12/1986 | Duthoy |
| 4,807,626 A | | 2/1989 | McGirr |
| 5,030,201 A | * | 7/1991 | Palestrant .................... 604/22 |
| 5,376,094 A | | 12/1994 | Kline |
| 5,376,100 A | * | 12/1994 | Lefebvre .................... 606/180 |
| 5,397,320 A | * | 3/1995 | Essig et al. .................. 606/127 |
| 6,174,318 B1 | * | 1/2001 | Bates et al. .................. 606/127 |

* cited by examiner

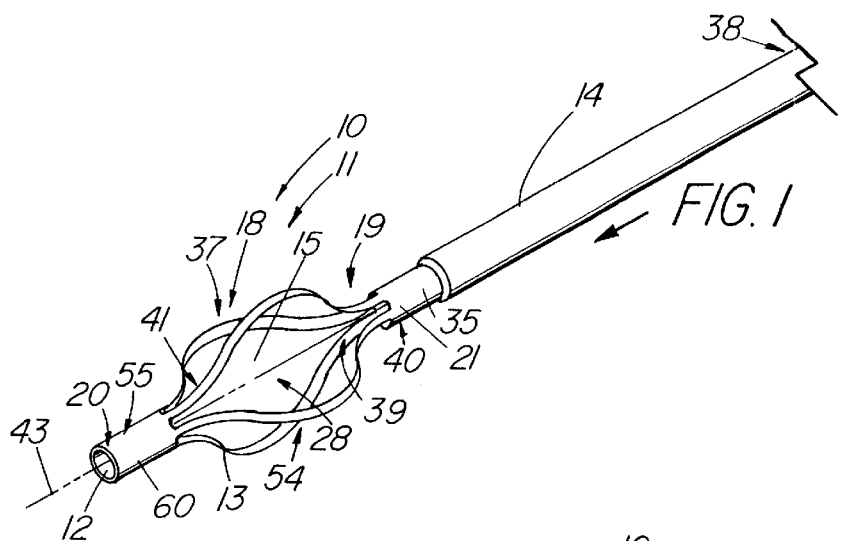
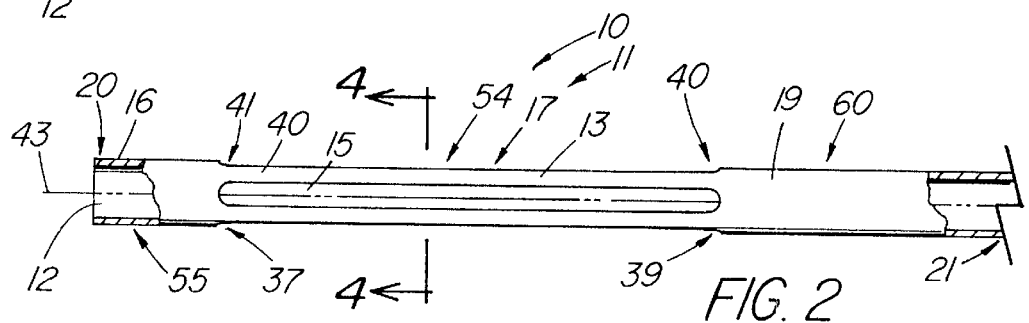
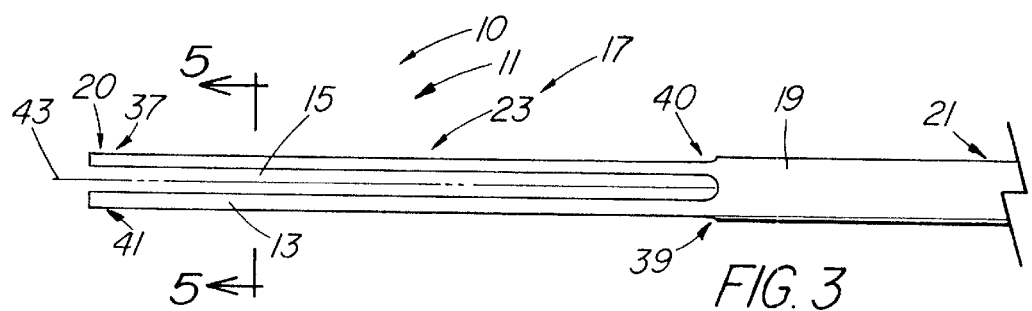
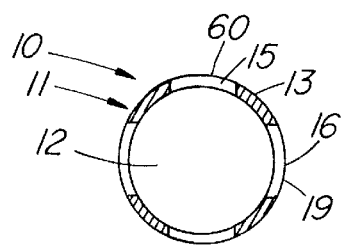
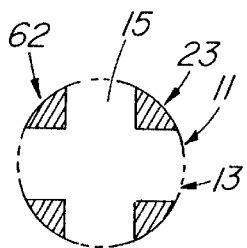
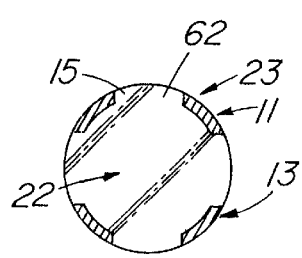

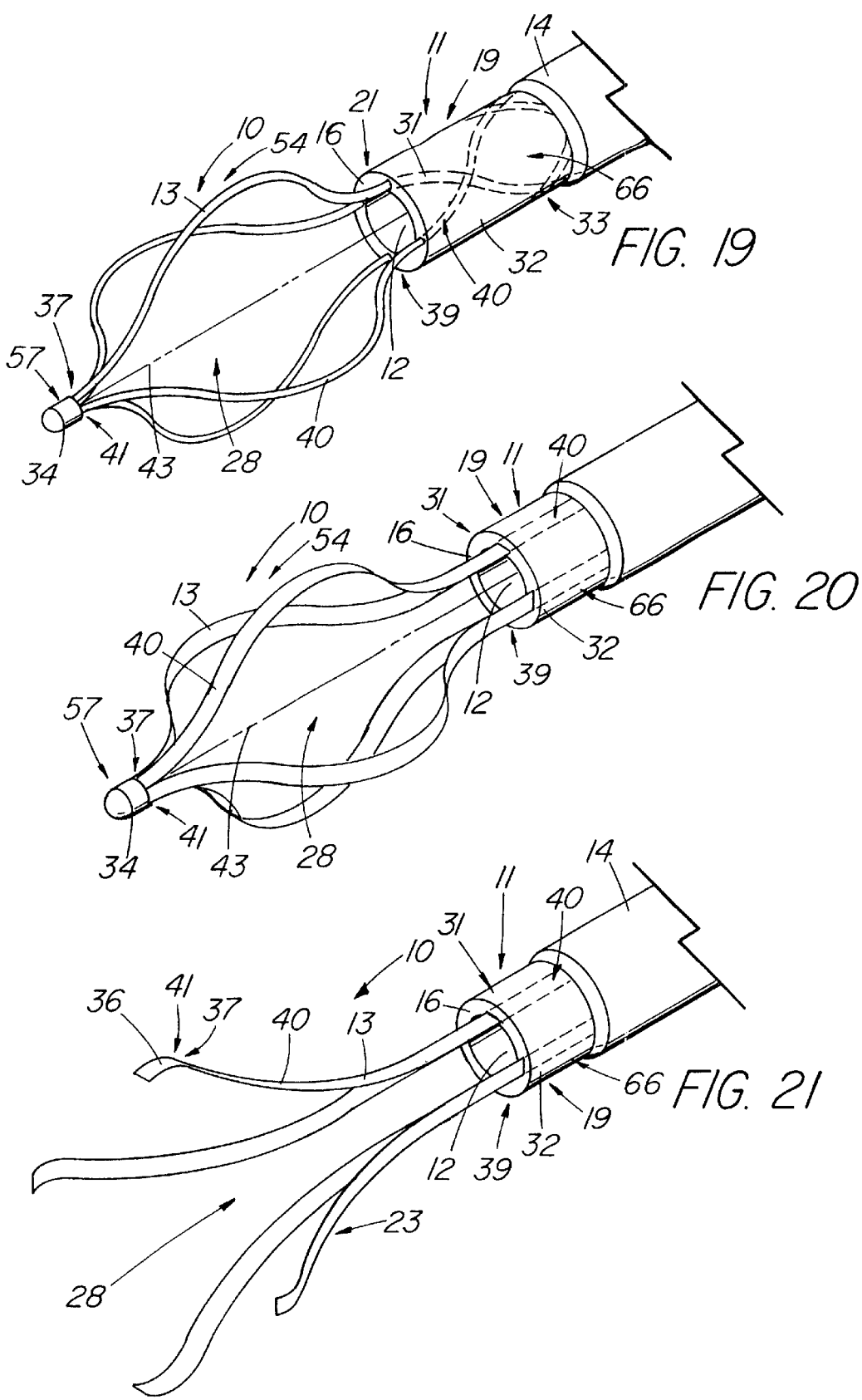

MINIMALLY-INVASIVE MEDICAL RETRIEVAL DEVICE

CROSS-REFERENCE TO RELATED APPLICATION

This application claims priority of provisional application Serial No. 60/079,540, filed Mar. 27, 1998.

TECHNICAL FIELD

This invention relates generally to medical devices, and in particular, to medical retrieval devices for engaging and/or removing objects, such as calculi and the like, from the body.

BACKGROUND OF THE INVENTION

Various organs and passages in the body are subject to the development of stones, calculi and the like. Gallstones are a common problem in the United States and are the most frequent cause of gallbladder inflammation. Calculi in other parts of the biliary system are also commonplace. Similarly, stones, calculi and the like can develop throughout the renal or urinary system, not only in the ureters and distal to them, but also in the renal tubules and in the major and minor renal calyxes. The calyxes are hollow collecting structures in the kidneys, extending from the renal pelvis, the minor calyxes in particular joining the renal pyramids. For simplicity, the calyxes can be considered as ducts extending from the connecting tubules of the renal nephrons to the ureters.

Minimally invasive surgical procedures have been developed for the removal of stones, calculi and the like from the biliary and urinary systems. Such procedures avoid the performance of invasive, open surgical procedures (such as, for example, the cholecystectomy) and can instead employ percutaneous access, in which stones, calculi and the like are removed through a percutaneously inserted access sheath. Several access routes are suitable, depending upon the specific system and the particular location in the system at which the stones, calculi or the like are found. Without regard to the access route, however, percutaneous removal is usually based upon the use of either forceps or basket-tipped catheters to engage and remove the stones, calculi, and the like.

A closed, wire tipped basket (helical or straight wire) permits entry of the stone or the like from the side of the basket, while an open ended basket allows a head-on approach to the stone or the like. Other retrievers and graspers can include forceps or can include a loop or snare for encircling the body to be removed, the loop or snare being made of, for example, round or flat wire. Flat wire has the advantage over round wire in that baskets incorporating flat wire exhibit better resistance to twisting during use. Moreover, while surgical techniques have advanced, and endoscope accessory channels of a relatively smaller diameter have been developed, efforts to reduce the diameter of round wires incorporated in stone extraction baskets have unfortunately not met with similar success. In practice, the lowest useful round wire diameter remains about 0.007 to 0.010 in. (about 0.178 to 0.254 mm). Because there is a significant amount of wasted space inside any sheath or cannula containing round or flat wires, this limit on useful wire diameter has prevented the development of useful stone extractors of small diameter, and in particular, of extractors having an outside diameter (that is, the diameter of the sheath or cannula containing the wires) below about 1.7 French (0.022 in. or 0.56 mm).

Another desirable feature of smaller retrieval devices, especially important for urological use, would be to have a device that works with a small diameter endoscope, such as an ureteroscope, that is capable of accommodating accessory instrumentation such as a laser fiber or hydraulic lithotripsy wire to break up stones or calculi for easier removal. The limited space and limited numbers of lumens available in the smaller scopes makes it advantageous to create devices that are capable of sharing the existing accessory channels of the endoscope without having to increase lumen diameter. While some small-diameter retrieval devices are capable of being introduced through a ureteroscope, the size and design of the wire precludes having an internal lumen through which accessory instrumentation, such that for performing a lithotripsy procedure, can be introduced into the workspace of the retrieval device.

SUMMARY OF THE INVENTION

The foregoing problems are solved and a technical advance is achieved in an illustrative medical retrieval device which is particularly useful with an endoscope for engaging or capturing and removing, extracting, or retrieving objects such as stones, calculi, concretions, foreign bodies and the like from a variety of locations in the body. The disclosed embodiments of the present medical retrieval device can each be characterized as being formed from a single elongated member wherein the resilient grasping members of the distal portion of the elongated member each represent a continuum of a material that essentially extends the length of the device. The resilient members form either a basket or a forceps.

In one embodiment of the present invention, the individual grasping members result from longitudinally slotting the elongated member about one end. The elongated member can be a hollow cannula or a solid member, preferably cylindrical in shape. The slots are formed by removing material of the elongated member in the form of longitudinal, elongated slots. The resilient grasping members result about the circumference of the elongated member with the remaining material thereof. Alternatively, the members result from the removal of material to expose elements, such as reinforcement wires, that are already encased within the walls of the elongated member. Advantageously, the members can comprise a basket or snare when the grasping members are interconnected at the distal end of the device, or grasping forceps when they are not.

Basket-making methodology has previously involved soldering, welding, crimping, or otherwise attaching the basket wires to a separate shaft piece. By having the wires or resilient grasping members being continuous with the proximal shaft portion of the device, any joint is advantageously eliminated. Such a joint can be more subject to breakage, possibly resulting in the dangerous situation of having a loose broken wire within the patient. Another advantage of a retrieval basket, grasper, or forceps of the present invention made from a thin-walled cannula or tube is the large open lumen and a small relative O.D. This large open lumen advantageously permits lithotripsy procedures to be performed when the retrieval device is inserted through an utereoscope. The present invention is particularly advantageous over the prior art in that the device can have an overall outside diameter significantly smaller than the outside diameter of existing retrieval or extraction devices, wherein the joint between wires and shaft increases the outer diameter and/or the available inner lumen diameter. The retrieval device of the present invention can have an outside diameter as small as 1 Fr., although 2–3 French is a preferred size for use in conjunction with a ureteroscope and laser fiber or lithotripsy laser fiber. Smaller devices will be able to reach deeper inside the body to capture and retrieve stones and calculi. It should go without saying that the smaller diameter is also expected to reduce the risk of patient discomfort and the risk of inadvertent damage to tissue during introduction and manipulation of the device in the patient.

Visualization of the target object is essential when using a retrieval device. Endoscopes, used in most minimally invasive procedures to retrieve stones or calculi, typically have a second or third accessory channel or lumen for introducing ancillary devices to the treatment site. The smaller diameter endoscopes, such as a ureteroscope, have a very narrow accessory channel through which the retrieval device is fed. An advantage of the present invention is that the tubular design, with its large central lumen, allows the introduction of additional instrumentation useful to the procedure such as a guidewire that may be used for placement, or a device to break up a stone or calculus such as a laser fiber or electrohydraulic lithotripsy wire. Conventional basket or grasper forceps manufacturing techniques that require soldering basket wires to the device shaft and/or compacting the basket wires into a narrow diameter do not leave sufficient additional room for other devices within the narrow working channel. While the central lumen is useful for introducing instruments into the inner working area, alternative embodiments include filling the end of the cannula with solder or another material to form a tip that is less traumatic to tissue.

An additional advantage of the present invention is the relative simplicity of construction. Devices comprised of a metal cannula or cylinder can be formed by making a series of longitudinal slots through the cannula/cylinder to form individual resilient grasping members. The process results in perfectly aligned grasping members and, except for reforming the grasping members, eliminates much of the skilled hand work normally required to assemble a basket or grasper forceps. Plastic deformation or heat setting the resilient grasping members into the outwardly extending configuration of a basket or forceps advantageously removes bending stresses and puts the expanded device in a relaxed condition during deployment. Retrieval devices of the present invention can use an external constraining mechanism such as a coaxial outer sheath or endoscope to open and close the resilient grasping members which capture and retain the target object for removal from a patient. Alternative methods could include an actuating member disposed in the lumen of the device to open and close the basket or grasper forceps.

In another embodiment of the present invention, the retrieval device is formed from an elongated member comprising a plastic tube having reinforcement wire encased therein. These wires, each representing a continuum of material extending the length of the elongated member, are exposed within the distal portion of the tube that interconnects them, where they are then formed into the resilient grasping members for making a retrieval basket or grasping forceps.

BRIEF DESCRIPTION OF THE DRAWING

FIG. 1 depicts a pictorial view of a medical retrieval device of the present invention;

FIG. 2 depicts a side view of the device of FIG. 1 in an unexpanded or compact state;

FIG. 3 depicts a side view of an alternative embodiment of the device of the present invention comprising a grasper forceps;

FIG. 4 depicts a cross-sectional view of the device of FIG. 2 taken along line 4—4;

FIG. 5 depicts a cross-sectional view of the device of FIG. 3 taken along line 5—5 of an embodiment of FIG. 3 formed from a solid member and showing wedge-shaped resilient grasping members;

FIG. 6 depicts a cross-sectional view of an alternative embodiment of FIG. 3 taken along line 5—5 of FIG. 3 in which the alternative embodiment is formed from a solid member having a distal end bore;

FIGS. 19–21 depict pictorial views of further embodiments of the present invention in which the resilient grasping members of the device include strips or wires of one material that have been exposed from within the walls of an other material tube.

DETAILED DESCRIPTION

Figure 7:
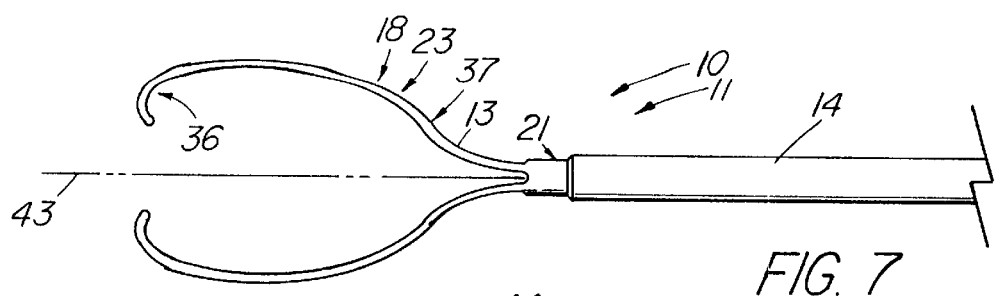
FIG. 7 depicts a side view of the device of FIG. 3 in an expanded state.

The medical retrieval device 10 of the present invention, as shown in FIG. 1, comprises an elongated member 11 that includes a distal portion 37 and a proximal portion 21. The distal portion includes a plurality of resilient grasping members 13 that are formed to provide a workspace volume 28 that provides the working space to capture and manipulate objects. The elongated cylindrical member 11 also includes a continuum of a first material 40 such as stainless steel which is a single continuous element, rather than being comprised of two or more distinguishable or connected elements of a single material (or different materials) that are soldered, crimped, or conjoined in some other manner. In the embodiments depicted in FIGS. 1–18, the continuum of first material comprises a single cannula 60 or a solid rod 62 from which medical retrieval device 10, such as a basket 54, grasping forceps 23, or snare 26, is formed. While it is preferable that a round or otherwise cylindrical cannula or rod is used, the elongated member 11 could have polygonalshaped cross-section. The continuum of first material 40 preferably is comprised of a suitable resilient material for forming the resilient grasping members. Any elastic material that can retain bending stresses and resiliently return to its preformed shape may be used. Metal is the preferred material for making a medical retrieval device 10 with the most preferred materials being stainless steel or an alloy having superelastic properties such as an alloy of nickel-titanium commercially available as nitinol (NiTi). The preferred stainless steel would be one in the 300 series with the 400 series also providing an alternative material. Certain polymer materials having a sufficient modulus of elasticity can also be used in larger sized devices. Superelastic materials like nitinol are preferred for the smallest devices (less than 4 Fr) with very thin wall thicknesses because of their improved resistance to fracture or kinking.

The preferred method of forming the resilient grasping members 13 from the elongated member is to remove material of the elongated member 11 by creating slots 15, open areas, or spaces therebetween the resilient grasping members 13. In the illustrative embodiment, four resilient grasping members 13 are formed from cannula 60 by the establishment of slots 15 through the walls 16 of elongated cylindrical member, in particular, the cannula 60.

FIG. 2 depicts a side view of the cannula 60, showing the distal portion 37 of retrieval device 10 prior to reshaping of the resilient grasping members is depicted in FIG. 2. FIG. 4 depicts a cross-sectional view of the device of FIG. 3 taken along line 4—4. Slots 15, equal in number to the desired resilient grasping members are incorporated into the wall 16 of the elongated member. When a hollow metal cannula 60 is used such as in the embodiment depicted, the unwanted material between the resilient grasping members 13 can be removed by a cutting means such as a standard EDM wire machine or a laser. Alternative methods include water jet, machining, or chemical etching. When a wire machine is used, a pilot hole for the continuous EDM wire is drilled through the elongated member 11. The diameter of the cutting wire or laser determines the diameter of the slots 15 and consequently, the width, thickness, and/or diameter of the resilient grasping members 13. An alternative method of cutting the slots into a cannula would be to insert a rod and then set a laser (or other cutting instrument with similar capabilities) to make a cut of predetermined depth which is prevented from extending through the opposite side of the cannula 60 by the inserted rod. Still another method would be to create the slots, spaces, or openings during initial fabrication of the elongated member 11, especially in the case of a device made of made of plastic. In the illustrative embodiment, the slots 15 terminate prior to the distal end 20 of the elongated member 11, leaving a distal closed cylinder 55 like the proximal closed cylinder 19 that comprises the proximal portion 21 and constitutes the handle or shaft of the basket 54. The distal closed cylinder 55 provides the means to unite the distal ends 41 of the resilient grasping members, eliminating the need for a separate connection such as solder joint or a crimping device.

Figure 17:
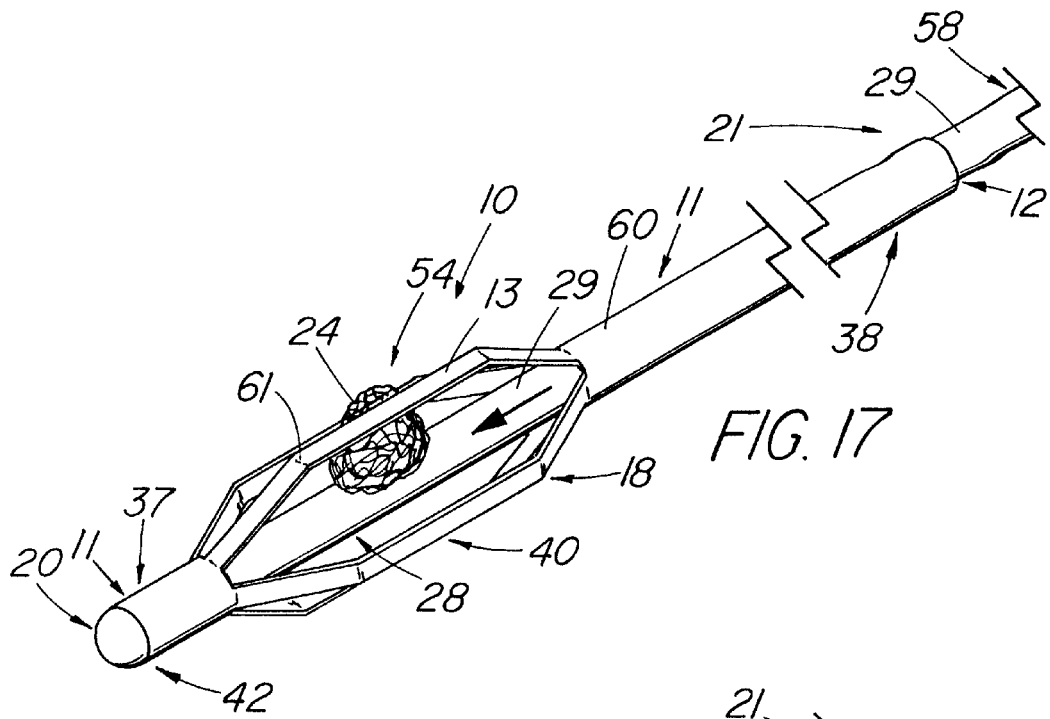
FIG. 17 depicts a pictorial view of still yet another alternative embodiment of the present invention in which the device includes an actuating member.

After the longitudinal slots 15 are initially formed, the resilient grasping members 13 have an compact shape 17 in which they are essentially parallel with the longitudinal axis 43 of the elongated member. In the cannula 60 embodiments, this produces an elongated member 11 with its original and maximal lumen size and essentially no increase in overall diameter of the retrieval device 10 while it is in the compact or compressed shape 17, as depicted in FIG. 4. Returning to FIG. 1, a basket 54 is formed by plastically deforming the individual resilient grasping 13 members into a second, outwardly projecting, expanded shape 18 such that a workspace volume 28 is created between the outwardly projecting grasping members in which calculi can be ensnared for retrieval or manipulation. The grasping members can be given any shape that creates an open region for capturing objects such as the arcuate shape of FIG. 1, or an angular shape created by introducing bends 61 in the resilient grasping members 13 as shown in the embodiment of FIG. 17.

If the retrieval device 10 of the present invention is to be made of nitinol, instead of stainless steel, the slots 15 are cut and resilient grasping members 13 are formed into the enlarged shape 18 using a mandrel or fixture to retain the shape. The device is then heat set or "trained" into the enlarged shape 18, wherein the bending stresses of resilient grasping members are removed. For example, the temperature for thermally setting the finished device may be 500° C. or higher. The transformation temperature, at which the material changes from the malleable martensitic state to the shape memory austenitic state must be below that at which the device is used so that the resilient grasping members retain their shape and have sufficiently resiliency to function as a retrieval device. This temperature can be set below room temperature, e.g., 10° C., or it may be set at a point between room temperature and body temperature so that the device may be easily loaded into the outer sheath while in a martensitic state. An alternative method of forming bends in nitinol is plastically deforming the material in a manner known as cold working. The nitinol is mechanically overstressed such that there is a localized phase change that results in a permanent bend at that site.

To affect opening and closing of the retrieval basket 54, an external restraining mechanism 14 such as a coaxial outer sheath is used as shown in FIG. 1. When it is important to minimize the overall size of the device, it is naturally important to select the smallest sheath 14 that permits axially movement over the elongated cylindrical member 11. To reduce friction between the elongated cylindrical member 11 and the external constraining mechanism 14, it is advantageous to add a thin layer 35 of lubricious material such as polytetrafluoroethylene (PTFE) to the outer surface of the elongated cylindrical member 11.

Figure 12:
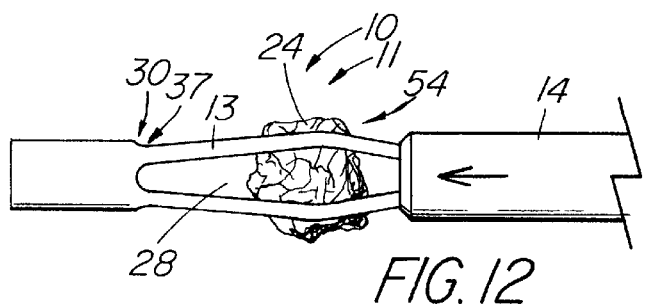
FIG. 12 depicts a side view of the device of FIG. 1 in a closed position with a captured calculus.

FIG. 12 depicts a side view of the device of FIG. 1 in the closed position 30 with a captured calculus 24. In the absence of a calculus 24 or other captured object, the substantially closed position 30 would be essentially the same as the compact position of FIG. 2. The external constraining mechanism 14 is advanced over the resilient grasping members 13, resiliently deforming and radially compressing the resilient grasping members 13 from the their proximal ends 39 until the resilient grasping members 13 firmly secure the calculus within the constricted workspace volume 28. If desired, the retrieval device 10 and the retrieved object 24 can then be removed from the body together.

FIG. 3 depicts a side view of an alternative embodiment of retrieval device 10 of FIG. 1 that comprises a set of grasper forceps 23 with the resilient grasping members 13 in the compact shape 17. A grasper forceps is essentially manufactured the same as the device of FIG. 1 with the exception that the slots 15 extend to the distal end 20 of the elongated member 11. As with the manufacture of baskets, the resilient grasping members are plastically deformed or heat set to an open position 18, as depicted in FIG. 7, for receiving an object from within a patient. To facilitate capture and retention of the object, the distal tips 36 of the resilient grasping members may be bent inward. The resilient grasping members close upon the target object by means of the external constraining mechanism 14 which is advanced in the same manner as with the basket 54 of FIG. 1.

Figure 8:
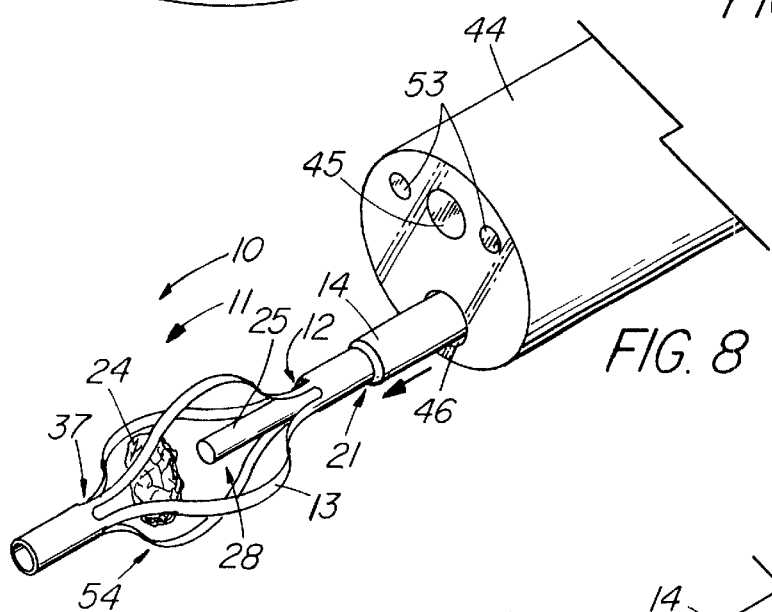
FIG. 8 depicts a pictorial view of the device of FIG. 1 being used with an endoscope to locate and break up a calculus.

FIG. 8 depicts a pictorial view of the retrieval device 10 of FIG. 1 showing how it may be used in combination with ureteroscope 44. For retrieval of calculi within the urinary tract, a standard ureteroscope 44 is typically used which includes an optical lens 45 connected to a series of lenses or optical fibers to permit visualization of the target, a light source 53 for illumination, and at least one accessory channel 46 for the introduction of instrumentation and/or the passage of fluids. The accessory channel 46 of a typical ureteroscope can range from 2.0 Fr up at least 6 Fr. The illustrative embodiment, which has an outer diameter of about 3 Fr, can be used with a 3.4 Fr accessory channel. The outer diameter of the compressed basket 54 or elongated cylindrical member 11 is about 2 Fr with the passage 12 about 0.066 mm in diameter. The passage 12 can accommodate a standard laser lithotripsy wire which is about 200 microns in diameter, excluding cladding. The laser delivers energy to the calculus 24, breaking it into smaller fragments that can be passed through the ureter or retrieved through the passage 12 of the device. While the use of a small size retrieval device 10 advantageously permits its passage through an endoscope, it is contemplated that larger basket or forceps embodiments of the present invention, such as 9 Fr or larger, can also be utilized for general retrieval applications in the body as well, especially where a large central lumen is desired.

A further benefit of forming retrieval device 10 from a cannula is the resulting semicircular cross-sectional shape of the resilient grasping members (as shown in FIGS. 4 and 6). Given a semicircular shaped resilient grasping member and a flat or bar shaped member of an identical size and material, an individual semicircular shaped resilient grasping member is shown empirically to be able to exert about 25 times more force inwardly against the target object. This demonstrated structural advantage is a similar to that of an I-beam which is used as a girder design in building construction due to its superior strength.

In addition to being made from a cannula, baskets and grasper forceps of the present invention can be fabricated from a solid elongated member. FIG. 5 depicts a cross-sectional view of elongated cylindrical member 11 taken along line 5—5 of an alternate embodiment of FIG. 3 formed from a solid member and having wedge-shaped resilient grasping members. The wedge-shaped grasping members depicted can be formed by creating two slots through the elongated member in essentially the same manner as with the embodiments made from a metal cannula. Baskets and graspers made from wedge-shaped grasping members are advantageously compressed into a smaller diameter than those of standard round or flat wire and are further disclosed by Bagley et al. in a co-pending provisional application by the present assignee entitled, "Minimally Invasive Retriever Including Wedge-Shaped Wires" filed Mar. 20, 1998 (Serial No. 60/078,290) which is incorporated herein by reference.

FIG. 6 depicts a cross-sectional view, looking proximally, of an alternative embodiment FIG. 3 in which the device has been formed from solid member 62, wherein the resilient grasping members 13 are essentially semicircular in shape. They are formed by creating a central bore 22 into the distal end 20 of the solid elongated member to a point at least near to where the proximal ends of resilient grasping members will be. The slots 15 are then formed to produce a grasper forceps of the compact shape 17, which are then formed into a enlarged shape 18 in the same manner as the embodiment of FIG. 7. The semicircular-shaped grasping members of the embodiment of FIG. 6 are of the same general shape as if formed from a cannula, although the central bore will not normally extend substantially or at all beyond the proximal ends of the resilient grasping members. Generally, graspers and baskets made from solid cylindrical stock would have a solid shaft or proximal portion 21 without a central lumen and therefore, would not be able to accommodate an additional instrument or device.

Figure 9:
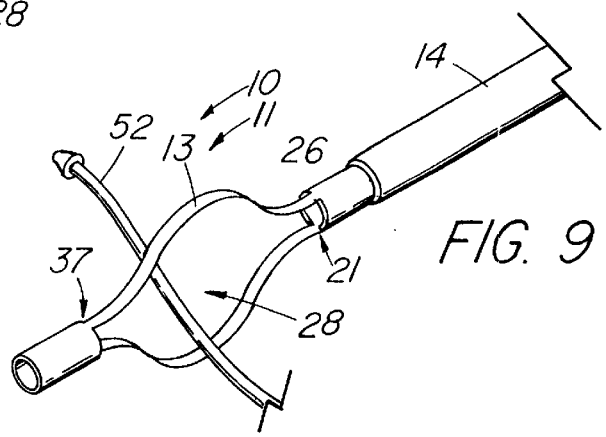
FIG. 9 depicts a pictorial view of an alternative embodiment of the device of the present invention comprising a snare.

The embodiments depicted in FIGS. 1–8 disclose retrieval devices having four resilient grasping members, however, devices having two to eight grasping members are feasible. FIG. 9 depicts a pictorial view of an alternate embodiment of retrieval device 10 of FIG. 1 having two resilient grasping members 13 formed by cutting a single slot. A retrieval device of this type can be especially useful as snare 26 for retrieving elongated foreign objects 52 such as catheters, pacemaker leads, etc.

Figure 13:
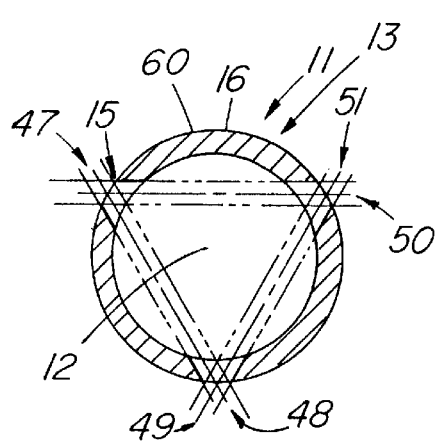
FIG. 13 depicts a cross-sectional view of an alternative embodiment of the present invention in which the device includes three resilient grasping members.

FIG. 13 depicts a cross-sectional view of an unexpanded alternate embodiment of the device of FIG. 1 having three resilient grasping members 13 formed by three slots 15. In this particular embodiment, the pathways that form the three slots 47; 48,49; and 50,51 create an imaginary triangle in cross-section. In this discussion, "slots" refer to an single longitudinal opening through the cannula wall, while "pathway" refers to an imaginary line passing through two different slots on the cannula, indicative of how the slot is formed. Therefore, a single slot may have two different element number designations (e.g., 48,49 and 50,51). The first slot 47 is formed through the elongated cylindrical member such that the resulting exit slot 48 lies 120° along the circumference of the cylinder with respect to the first entrance slot 47, rather than diametrically opposed as with devices having an even number of grasping members. To create a third slot 50, a second entrance slot 49 is formed whereby either the entrance slot 49 or second exit slot 51 is the same as either the first entrance slot 47 or first exit slot 48 which are already formed. For example, a second pathway 49–51 can be precut through the first exit slot 48 for the EDM wire to create a second exit slot 51 120° from the second entrance slot 49/first exit slot 48, and 120° from the first entrance slot 47. An optional third entrance slot 50 can be made through the second exit slot, passing through the first entrance slot to finish the edges in a uniform manner, however, these two slots will have already been formed. This method is not limited to a device having three grasping members. For example, a device having five grasping members would require that the slots be formed at 72° intervals along the circumference of the cylinder with slot pathways forming an imaginary pentagon. An alternate method of forming an odd number of slots would be the technique described above in which a rod is inserted, and the slots are cut at the desired intervals, rather than two being formed with a single cut.

Figure 14:
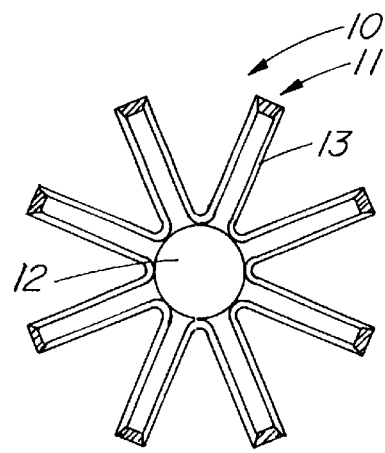
FIG. 14 depicts a cross-sectional view of an other alternative embodiment of the present invention having eight resilient grasping members.

FIG. 14 depicts a cross-sectional view of an expanded alternate embodiment of retrieval device 10 of FIG. 1 having eight resilient grasping members 13. Such a basket would be advantageous for capturing and retaining smaller objects.

Figure 10:
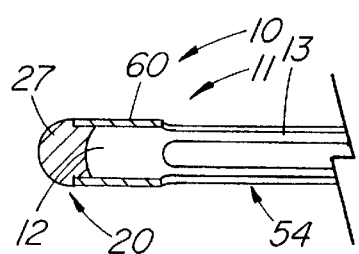
FIGS. 10–11 depict side views of alternative embodiments of the device of the present invention wherein the distal end of the device includes a solid tip.

FIG. 10 depicts a side view of an alternate embodiment of retrieval device 10 of FIG. 1 wherein the distal end 20 is soldered closed. The solder joint 27 within the tip is finished by grinding and/or polishing. The polished tip helps prevent trauma to delicate tissues during use of the device. Closing the distal end does not interfere with feeding a laser fiber or other device through the lumen to treat an ensnared calculus, however, an open distal end would be advantageous if the capability to feed the device over a guidewire is desired.

Figure 11:
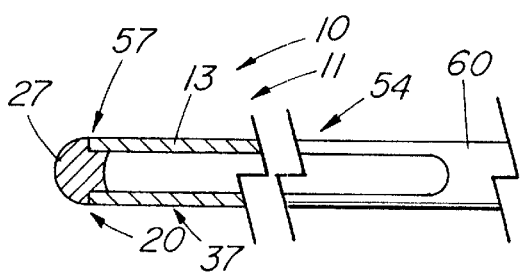

FIG. 11 depicts a side view of an alternate retrieval basket 54 of device 10 of FIG. 1, wherein rather than a distal cylinder 55 (intact portion of cannula 60) interconnecting the distal ends 41 of the resilient grasping members 13, a fastener 57 such as a solder joint 27 is used. As used herein, fastener 57 can comprise any well-known method of joining the resilient grasping members such as a cap, crimp, band, weld (including spot weld), or adhesive. This method of joining the resilient grasping members 13 provides an alternate method of creating a retrieval basket 69 whereby the elongated member 11 can be cut the same as the grasping forceps 23 embodiments depicted in FIG. 3.

Figure 15:
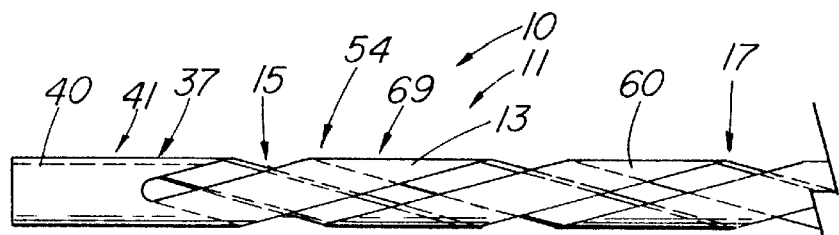
FIG. 15 depicts a side view of yet another alternative embodiment of the present invention in which the device includes a helical retrieval basket.
Figure 16:
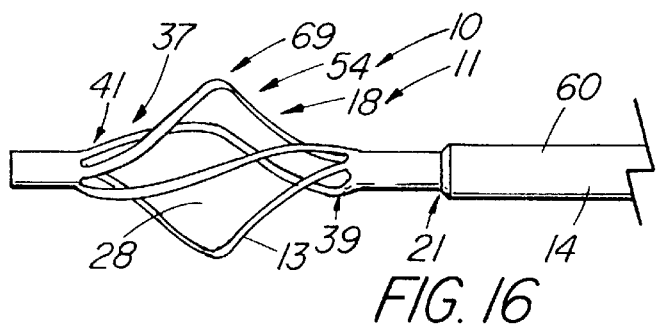
FIG. 16 depicts a side view of the device of FIG. 15 in an expanded state.

FIGS. 15–16 depict another preferred embodiment of the present invention in which the resilient grasping members 13 of retrieval device 10 are formed to produce a helical medical retrieval basket 10. FIG. 15 is a side view of an unexpanded four-wire helical basket 54 having spiral-shaped slots 15. The slots 15 can be formed in a similar manner to the embodiment of FIG. 1, the difference being that either the cutting means or the cannula 60 itself is rotated to produce slots 15 that spiral around the circumference of the cannula 60. This method of manufacture can also be adapted for use with solid wire. FIG. 16 depicts a side view of medical retrieval device of FIG. 15. As with the non-helical embodiments the resilient grasping members 13 are manually formed into the enlarged shape 18 where the grasping members 13 are in a relaxed, non-stressed state or condition.

Figure 18:
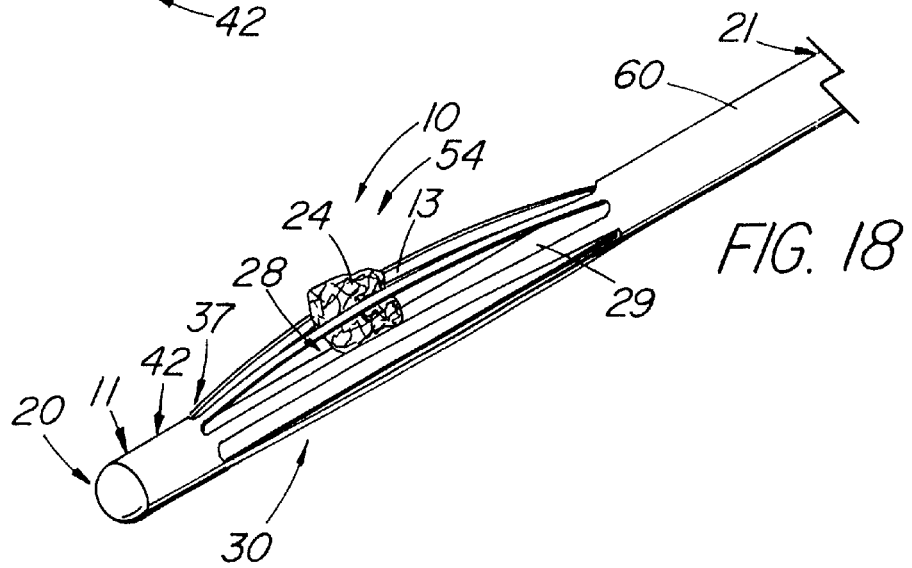
FIG. 18 depicts a pictorial view of the device of FIG. 16 in a closed position.

FIGS. 17–18 depicts a pictorial view of alternate embodiment of device 10 of FIG. 1 that includes an actuating member 29 rather than an external constraining mechanism, for opening the basket to receive a calculus 24. FIG. 18 depicts a pictorial view of retrieval device 10 of FIG. 16 in which the actuating member 29 has been advanced to close the resilient grasping members 13 over the calculus 24. The distal end 42 of actuating member 29 is soldered or otherwise attached to the distal end 20 of device 10. While the unexpanded device is contained within an endoscope or introducer sheath, the actuating member 29 is in its fully advanced position. When the grasping members 13 have been exposed, the basket 54 is manipulated into the open or enlarged shape 18 by pulling back on the actuating member 29 which then can be locked into position. To close the basket, the actuating member 29 is fully advanced to the substantially closed position 30, ensnaring the calculus 24. The actuating member 29 may be locked into position at the proximal end 38 of the device by a locking hub or other well-known means to prevent accidental release of the calculus 24 while it is withdrawn from the body.

While the actuating member does somewhat restrict the size of the workspace volume 28 available to receive a calculus, it eliminates the outer sheath, thereby allowing the device to occupy a smaller lumen or reach a more restricted space than would a coaxial device having the same diameter retrieval basket 54. The small-diameter actuating member may be used to still permit space within the lumen for additional instrumentation, or a second lumen could be reserved in the elongated member 11 for that purpose. It is important that the actuating member 29 must be of sufficient stiffness during advancement to force closure of the resilient grasping members without significant lateral flexure of the rod. Because the position of the actuating member 29 relative the cannula 60 controls whether the basket is open or closed, the resilient grasping members 13 could be in the relaxed, non-stressed state while either in the enlarged shape, as with the other embodiments, or in the compact shape. In the case of the latter withdrawing the actuating member 29 relative the cannula 60 opens the basket into the enlarged shape 18, while advancing actuating member will return the resilient grasping members 13 to the relaxed compact shape 17.

FIGS. 19–21 depict other preferred embodiments of retrieval device 10 of the present invention whereby the continuum of a first material 40 that comprises the resilient grasping members 13 can include a plurality of reinforcement wires 31 that are interconnected by an other material 66 in the proximal portion 21 of elongated member 11. In the illustrative embodiments, the retrieval device 10 comprises a plastic tube 32 having flat resilient metal or plastic reinforcement wires 31 encased within the walls 16. By removing a portion of the plastic tube 32 in the distal portion 37 of the elongated member 11, the exposed reinforcement wires 31 function as resilient grasping members 13 after they are formed into the enlarged shape 18.

FIG. 19 depicts a retrieval basket 10 in which the resilient grasping members 13 are flat reinforcement wires 31 having a helical braid pattern 33 while encased in plastic tube 32. The resilient grasping members 13 can be redirected or straightened as they exit distal end 56 of the plastic tubing 32, or follow the natural contour of helical braid 33. It is possible to have fewer resilient grasping members 13 than exposed reinforcement wires 31 by truncating some of wires at the tube distal end 56 where they exit the tubing 32. In an example of a reinforced tube with eight braided wires, all helical wires of one direction (e.g., spirally clockwise) can be truncated, leaving four exposed wires spiraling the other direction for which to form a four-member helical basket. The distal ends 41 can be joined with a fastener 57 such as an end cap 34 or other well-known means. Another alternative of making a retrieval basket 54 is to leave a portion of the original plastic tube 32 at the distal end similar to distal cylinder 55 in FIG. 1 to interconnect the distal ends 41 of the resilient grasping members 13.

FIG. 20 depicts another preferred embodiment of the present invention whereby the reinforcement wires 31 are aligned with longitudinal axis 43 of the elongated member 11, rather than being helical wound. This type of basket would not normally require redirection or truncation of wires as they exit the distal end of the plastic tube 32.

FIG. 21 depicts an embodiment of the devices of FIGS. 18 and 19 in which the unsecured resilient grasper elements comprise grasper forceps 23. The distal ends 41 of the resilient grasping members 13 can be deformed inward to facilitate capture and retention of a target object.

The retrieval device 10 of the present invention preferably comprises medical grade materials which can be sterilized by conventional procedures prior to use. Conveniently, the retrieval device 10 can be made of relatively inexpensive synthetic and metallic materials, so that the device 10 can be disposed of after a single use, rather than being resterilized and reused. Such reuse, however, is also contemplated within the scope of the invention.

Of course, these and the other details of construction can be changed to adapt the retrieval device 10 of the present invention to the particular surgical technique to be performed.

It should be clear from the foregoing disclosure that the retrieval device 10 of the present invention is particularly advantageous over prior devices in a variety of ways. Most important, the present invention is particularly advantageous over the prior art in that the device (and in particular, its outer sheath) can have an overall outside diameter significantly smaller than the outside diameter of existing retrieval or extraction devices. Indeed, the retrieval device of the present invention can have an outside diameter as small as 1 FR (0.33 mm). The retrieval device of the present invention is expected to allow the capture, removal, extraction and/or retrieval of stones, calculi, concretions, foreign bodies and the like from locations in the body much deeper than can be achieved with existing devices. The basket, grasper or other engagement means formed from the wedge-shaped wires enjoys the good resistance to twisting and bending, despite this small diameter, and as noted in the preferred embodiment of the invention is capable of being formed and maintained in a helical shape, just like round wires. The smaller overall diameters enjoyed by the present invention should also reduce the risk of patient trauma during use.

As noted above, the retrieval device of the present invention is expected to find use in a wide variety of procedures, including urological procedures, biliary procedures, vascular procedures and procedures for the retrieval of foreign objects from a variety of body cavities. Moreover, retrieval devices of the present invention formed from a cannula or tube offer the ability to introduce a laser fiber or other treatment device, or feed the retrieval device over a guide wire to facilitate placement within the body.

The details of the construction or composition of the various elements of the retrieval device 10 not otherwise disclosed are not believed to be critical to the achievement of the advantages of the present invention, so long as the elements possess the strength or flexibility needed for them to perform as disclosed. The selection of any such details of construction is believed to be well within the ability of one of even rudimentary skills in this area, in view of the present disclosure.

What is claimed is:

1. An elongated medical retrieval device comprising:
   an elongated cylindrical member having a proximal end, a distal end, a proximal portion and a distal portion, the elongated cylindrical member comprising a first continuum of a first metallic material extending therealong;
   the proximal portion of the elongated cylindrical member including a proximal closed cylinder, the proximal closed cylinder comprising the continuum of first metallic material and having a circumferential wall of substantially uniform thickness;
   the distal portion forming a plurality of resilient grasping members, the resilient grasping members manipulable between a compact shape and an enlarged shape, wherein resilient grasping members of the enlarged shape are in a relaxed condition, and wherein the edges of adjacent resilient grasping members are spaced apart when in the compact condition, and wherein the resilient grasping members, each having a distal end and a proximal end are conjoined about the distal ends thereof; and
   an external cylinder of a second continuum of material to constrain the distal portion of the elongated cylindrical member in to the compact shape, the external cylinder being longitudinally slidable about the elongated cylindrical member to alternately deploy the resilient grasping members to the enlarged shape, or recompress the resilient grasping members having the enlarged shape into one of the compact shape or a substantially closed position for capture or capture and retrieval of an object from within a patient.

2. The device of claim 1, wherein the elongated cylindrical member further contains a passage extending longitudinally therein.

3. The device of claim 1, wherein the resilient grasping members are conjoined at the distal ends thereof by a distal closed cylinder further comprising the continuum of first metallic material.

4. A medical retrieval device comprising:
   an elongated cylindrical member having a proximal end, a distal end, a proximal portion and a distal portion, the elongated cylindrical member including a proximal closed cylinder, the closed cylinder comprising a continuum of a first metallic material extending therealong and having a circumferential wall of substantially uniform thickness;
   the distal portion forming a plurality of resilient grasping members formed from the continuum of fist metallic material, the resilient grasping members manipulable between a compact shape and an enlarged shape, wherein the resilient grasping members of the enlarged shape are in a relaxed condition, wherein edges of adjacent resilient grasping members are spaced apart when in the compact condition, wherein the resilient grasping members include space therebetween configured for insertion of an object therethrough, and wherein the resilient grasping members, each having a distal end and a proximal end are conjoined about the distal ends thereof.

5. The medical retrieval device of claim 4, wherein the resilient grasping members further comprise tips made from a different material.

6. The device of claim 4, wherein the resilient grasping members are conjoined at the distal ends thereof by a distal closed cylinder further comprising the continuum of metallic material.

7. The device of claim 4, further comprising an external constraining mechanism to constrain the distal portion of the elongated cylindrical member into the compact shape, the external constraining mechanism being longitudinally slidable about the elongated cylindrical member to alternately deploy the resilient grasping members to the enlarged shape, or recompress the resilient grasping members having the enlarged shape into one of the compact shape or a substantially closed position for capture or capture and retrieval of an object from within a patient.

8. A medical retrieval device comprising:
   an elongated cylindrical member having a proximal end, a distal end, a proximal portion and a distal portion, the elongated cylindrical member comprising a single continuum of a metallic material extending therealong;
   the proximal portion of the elongated cylindrical member including a proximal closed cylinder, the proximal closed cylinder comprising the continuum of metallic material and having a circumferential wall of substantially uniform thickness; and
   the distal portion forming a plurality of resilient grasping members, the resilient grasping members comprising the continuum of metallic material and manipulable between a compact shape and an enlarged shape, wherein edges of adjacent resilient grasping members are spaced apart when in the compact shape, and wherein the resilient grasping members, each having a distal end and a proximal end, are conjoined about the distal ends thereof.

9. The device of claim 8, wherein the elongated cylindrical member contains a passage therein.

10. A medical retrieval device comprising:
    an elongated cylindrical member having a proximal end, a distal end, a proximal portion and a distal portion, the elongated cylindrical member containing a passage therein and including at least one continuum of a first metallic material extending therealong;

the proximal portion of the elongated cylindrical member including a proximal closed cylinder, the proximal closed cylinder comprising the continuum of first metallic material and having a circumferential wall of substantially uniform thickness;

the distal portion including a plurality of resilient grasping members, the resilient grasping members comprising the continuum of first metallic material and manipulable between a compact shape and an enlarged shape, wherein edges of adjacent resilient grasping members are spaced apart when in the compact shape, and wherein the resilient grasping members, each having a distal end and a proximal end, are conjoined about the distal ends thereof; and an external constraining mechanism to constrain the distal portion of the elongated cylindrical member into the compact shape, the external constraining mechanism being longitudinally slidable about the elongated cylindrical member to alternately deploy the resilient grasping members to the enlarged shape, or recompress the resilient grasping members having the enlarged shape into one of the compact shape or a substantially closed position for capture or capture and retrieval of an object from within a patient.

11. A medical retrieval device comprising:

an elongated cylindrical member having a proximal end, a distal end, a proximal portion and a distal portion, the elongated cylindrical member including a proximal closed cylinder, the proximal closed cylinder comprising a single continuum of a metallic material extending therealong and further containing a passage therein;

the proximal portion of the elongated cylindrical member including the proximal closed cylinder, the proximal closed cylinder comprising the continuum of metallic material and having a circumferential wall of substantially uniform thickness;

the distal portion including at least three resilient grasping members formed from the continuum of metallic material, the resilient grasping members forming a retrieval basket, wherein the proximal end of each resilient grasping member is circumferentially offset from the distal end thereof such that the medical retrieval device is a helical basket, the retrieval basket manipulable between a compact shape and an enlarged shape, wherein the resilient grasping members of the enlarged shape are in a relaxed condition, wherein edges of adjacent resilient grasping members are spaced apart when in the compact condition, wherein the resilient grasping members include space therebetween configured for insertion of an object therethrough, wherein the resilient grasping members are configured to create a workspace volume for engaging an object therein, and wherein the resilient members each having a distal end and a proximal end, are conjoined about the distal ends thereof; and an external constraining mechanism to constrain the distal portion of the elongated cylindrical member into the compact shape, the external constraining mechanism being longitudinally slidable about the elongated cylindrical member to alternately deploy the resilient grasping members to the enlarged shape, or recompress the resilient grasping members having the enlarged shape into one of the compact shape or a substantially closed position for capture or capture and retrieval of an object from within a patient.

12. A medical retrieval device, comprising:

a continuum of a metallic material comprising a first cylindrical member at a proximal end and a second cylindrical member at a distal end of the continuum, said cylindrical members separated by a plurality of resilient grasping members, wherein the cylindrical members have a circumferential wall of substantially uniform thickness, the resilient grasping members are manipulable between a compact shape and an enlarged shape, and wherein the resilient grasping members of the enlarged shape are in a relaxed condition and wherein edges of adjacent resilient grasping members are spaced apart when in the compact shape.

13. The device of claim 12, further comprising a passage extending longitudinally through the first and second cylindrical members.

14. The device of claim 13, wherein an outer diameter of the continuum is as small as 0.33 mm.

15. The device of claim 13, wherein the passage extending longitudinally is at least 200 microns in diameter.

16. The device of claim 12, further comprising an external constraining mechanism longitudinally slidable about the continuum to deploy the resilient grasping members to the enlarged shape or to recompress the resilient grasping members to the compact shape or to a substantially closed position for capture or capture and retrieval of an object from within a human body.

17. The device of claim 12, wherein the resilient grasping members are aligned parallel with a longitudinal axis of the continuum or arranged in a spiral between the first cylindrical member and the second cylindrical member.

18. A method of using a medical retrieval for retrieving an object within a human body, the method comprising:

providing the device of claim 12; manipulating the resilient grasping members to an enlarged shape for capturing the object; and manipulating the resilient grasping members to a compact shape for grasping the object.

* * * * *

UNITED STATES PATENT AND TRADEMARK OFFICE
CERTIFICATE OF CORRECTION

PATENT NO. : 6,500,182 B2
DATED : December 31, 2002
INVENTOR(S) : Thomas L. Foster It is certified that error appears in the above-identified patent and that said Letters Patent is hereby corrected as shown below:

Title page,
Item [52], References Cited, FOREIGN PATENT DOCUMENTS, delete "07430456" and substitute -- 07430456 A1 -- in its place.
Item [57], ABSTRACT,
Line 1, after "retrieval" insert -- device --.

Signed and Sealed this

Twenty-first Day of October, 2003

JAMES E. ROGAN
*Director of the United States Patent and Trademark Office*

UNITED STATES PATENT AND TRADEMARK OFFICE
CERTIFICATE OF CORRECTION

PATENT NO.     : 6,500,182 B2
DATED          : December 31, 2002
INVENTOR(S)    : Thomas L. Foster It is certified that error appears in the above-identified patent and that said Letters Patent is hereby corrected as shown below:

<u>Title page,</u>
Item [56], References Cited, FOREIGN PATENT DOCUMENTS, delete "07430456" and substitute -- 0743046 A1 -- in its place.

Signed and Sealed this

Twenty-fifth Day of November, 2003

JAMES E. ROGAN
*Director of the United States Patent and Trademark Office*